(12) United States Patent
Dunn et al.

(10) Patent No.: US 7,459,067 B2
(45) Date of Patent: Dec. 2, 2008

(54) SEMI-PERMANENT REFERENCE ELECTRODE

(75) Inventors: Darrell S. Dunn, San Antonio, TX (US); Christopher Sean Brossia, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 465 days.

(21) Appl. No.: 10/799,247

(22) Filed: Mar. 12, 2004

(65) Prior Publication Data
US 2008/0128294 A1 Jun. 5, 2008

Related U.S. Application Data

(60) Provisional application No. 60/466,128, filed on Apr. 28, 2003.

(51) Int. Cl.
*G01N 27/26* (2006.01)
(52) U.S. Cl. .................. 204/435; 204/433; 204/196.36; 204/196.37; 205/734; 205/740
(58) Field of Classification Search ................. 204/433, 204/435, 196.36, 196.37; 205/734, 740
See application file for complete search history.

(56) References Cited

U.S. PATENT DOCUMENTS

| | | | |
|---|---|---|---|
| 3,582,531 A * | 6/1971 | Sheelor | 174/6 |
| 4,080,565 A | 3/1978 | Polak et al. | |
| 4,116,798 A | 9/1978 | Magar et al. | |
| 4,179,349 A | 12/1979 | Park | |
| 4,240,892 A | 12/1980 | Riggs, Jr. | |
| 4,504,365 A | 3/1985 | Kellner | |
| 4,601,810 A * | 7/1986 | Tiwari et al. | 204/413 |
| 4,806,850 A | 2/1989 | Saumade et al. | |
| 5,712,559 A | 1/1998 | Moore et al. | |
| 6,132,593 A | 10/2000 | Tan | |
| 6,193,865 B1 | 2/2001 | Hodges et al. | |
| 6,328,877 B1 * | 12/2001 | Bushman | 205/775 |

FOREIGN PATENT DOCUMENTS

CH 680022 A5 5/1992

OTHER PUBLICATIONS

Panoch, Miroslav, Semler, Miloslav, Kolinsky, Miloslav, Manek Bretislav Membrane for Calcuim Ion—Selective Electrode 1991, 7pp.

(Continued)

*Primary Examiner*—Bruce F Bell
(74) *Attorney, Agent, or Firm*—Gunn & Lee, P.C.

(57) ABSTRACT

A semi-permanent reference electrode for use in monitoring and measuring metals in field applications, such as cathodic protection. This electrode has an outer electrode body with a cap and porous plug. The outer electrode body is filled with a fill solution which is a saturated salt solution formed from a solid salt. The solid salt is hygroscopic with a low deliquescence point. An opening is provided in the cap to allow moisture into the outer electrode body to combine with the fill solution to maintain the saturated salt solution in the field. This saturated salt solution must maintain a constant pH for use in the semi-permanent reference electrode. A wire is used within the outer electrode body which connects to a voltmeter. This voltmeter measures the potential difference between the reference electrode and the field component of interest, which can include pipelines, storage tanks and bridges.

11 Claims, 2 Drawing Sheets

OTHER PUBLICATIONS

Tomasz Sokalski, Magdalena Maj-Zurawska, Adam Hulanicki, Andrzej Lewenstam Optimitation of a Reference Electrode with Constrained Liquid Junction for the Measurements of Ion. Electroanalysis 1999, 11, No. 9 Wiley-VCH Verlag Gmbh, D-69469 Weinheim, 1999.

Friedrich Oehme, Gorwihl Liquid Electrolyte Sensors: Potentiometry, Amperometry, and Conductometry Except from "Sensors—A Comprehensive Survey" Part I, 1991.

* cited by examiner

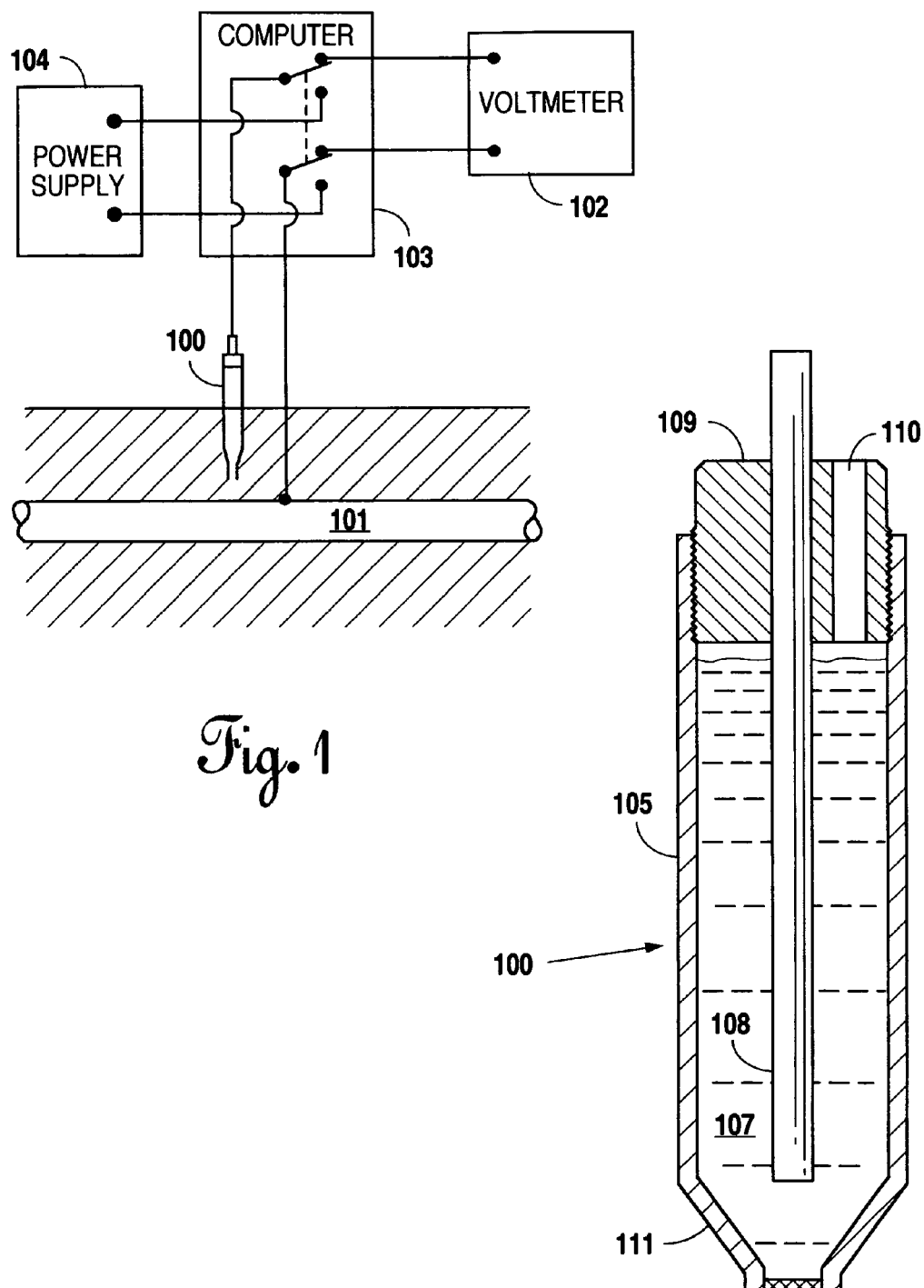

1

SEMI-PERMANENT REFERENCE ELECTRODE

Applicant claims priority under 35 U.S.C. §119 of U.S. Provisional Application Ser. No. 60/466,128 filed Apr. 28, 2003.

This is a provisional patent application, filed under 37 C.F.R.1.53(b)(2).

BACKGROUND OF THE INVENTION

1. Field of The Invention

Applicant's invention relates to a stable field-deployable reference electrode to facilitate potential measurements such as in corrosion sensing and monitoring.

2. Background Information

Presently, monitoring and measurement of the potential of metals in various environments is used in a broad array of industries, including cathodic protection of structures such as pipelines, storage tanks and bridges. The main limitations associated with reference electrodes are their short in-service life and the need for replacement/replenishment of the reference fluid within the reference cell. Some reference electrodes are used in field applications, the most common being the copper/copper-sulfate reference electrode. Though it can be used to provide a suitable reference point with which to make a measurement, copper sulfate reference electrodes cannot be left in the field over an extended period of time without significant maintenance. Thus, these reference electrodes need to be positioned in such a way to facilitate access, which is not always optimal with respect to the location where the measurement needs to be taken. Thus, there exists a need to have a more stable, lower maintenance reference electrode. Such an electrode would enable semi-permanent placement for in-field applications without high levels of maintenance.

SUMMARY OF THE INVENTION

It is an object of the present invention to provide a novel semi-permanent reference electrode.

Another object of the present invention is to provide a novel semi-permanent reference electrode that incorporates an outer electrode body, cap, porous plug, wire and fill solution that can be utilized in field applications.

Still another object of the present invention is to provide a novel semi-permanent reference electrode that incorporates a fill solution that can be maintained at a field location due to the presence of moisture in the field.

Yet another object of the present invention is to provide a novel semi-permanent reference electrode wherein the fill solution is a saturated salt solution.

It is another object of the present invention to provide a novel semi-permanent reference electrode wherein the solid salt used to form the fill solution is both hygroscopic and has a low deliquescence point.

An additional object of the present invention is to provide a novel semi-permanent reference electrode wherein the fill solution has a constant pH.

It is still another object of the present invention to provide a novel semi-permanent reference electrode wherein the cap has an opening passing from the external environment to the internal environment of the outer electrode body to allow moisture into the outer electrode body to combine with the solid salt to maintain the fill solution.

Yet an additional object of the present invention is to provide a novel semi-permanent reference electrode with the wire having the ability to maintain a relatively stable reference point in various field environments as well as in the saturated salt solution.

It is another object of the present invention to provide a novel semi-permanent reference electrode wherein the solid salt of the fill solution is hydrolyzable.

In satisfaction of these and related objectives, Applicant's present invention provides a semi-permanent reference electrode for use in monitoring and measuring metals in field applications, such as cathodic protection. This electrode has an outer electrode body with a cap and porous plug. The outer electrode body is filled with a fill solution which is a saturated salt solution formed from a solid salt that is hygroscopic with a low deliquescence point. When the fill solution dries out, it draws moisture from the environment to maintain the solution. An opening is provided in the cap to allow moisture into the outer electrode body to maintain the solution. This fill solution must maintain a constant pH for use in the reference electrode. A wire is used within the outer electrode body which connects to a voltmeter. This voltmeter measures the potential difference between the reference electrode and the field component of interest, which can include pipelines, storage tanks and bridges.

BRIEF DESCRIPTION OF THE DRAWINGS

FIG. 1 is a perspective view of the preferred embodiment of the present invention as it would exist in a field application.

FIG. 2 is a cross section of the preferred embodiment of the present invention.

DETAILED DESCRIPTION OF THE PREFERRED EMBODIMENT

Figure 3:
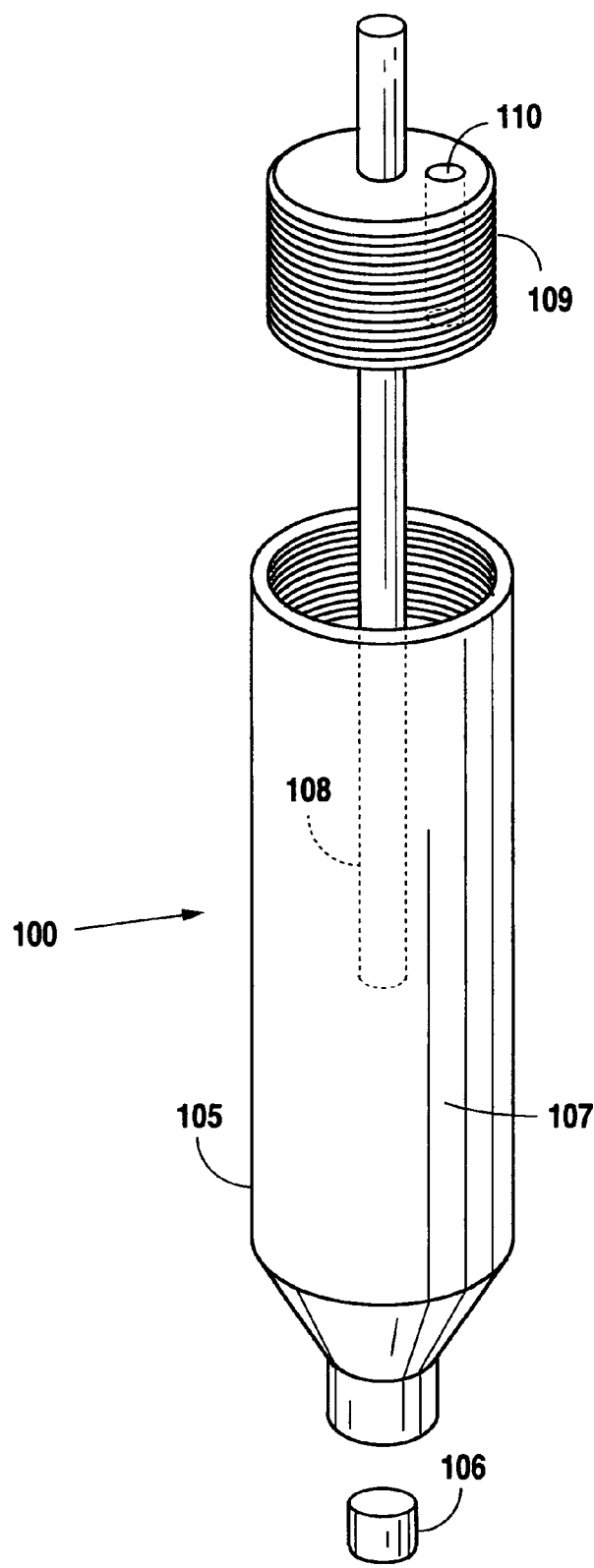
FIG. 3 is an exploded view of the preferred embodiment of the present invention.

Referring to FIG. 1, a perspective view of the preferred embodiment of the present semi-permanent reference electrode 100 as it would exist in a field application is shown. Semi-permanent reference electrode 100, with constant potential, is used in measuring the potential of the working electrode, which is where electrochemical reactions being studied occur. The semi-permanent reference electrode 100 and the working electrode together make up a cell. In corrosion testing the working electrode can be the metal itself, which for purposes of FIG. 1 will be the pipe 101. Semi-permanent reference electrode 100 allows for repeatability in the potential measurement.

The present semi-permanent reference electrode 100 can be used for determining the rate of corrosion or the extent of cathodic protection of a metallic object, such as the pipe 101, in a system that utilizes a voltmeter 102. Semi-permanent reference electrode 100 is placed on the earth's surface directly above the pipe 101. Semi-permanent reference electrode 100 is connected to the positive terminal of a voltmeter 102, the negative terminal of the voltmeter 102 being connected to pipe 101. Voltmeter 102 measures the potential difference between the pipe 101 and the semi-permanent reference electrode 100 to determine the corrosion potential.

To determine the extent of cathodic protection of pipe 101, direct current flow is produced onto pipe 101 for cathodic protection. This cathodic protection reduces the rate of corrosion by shifting the corrosion potential of the pipe 101, or other metallic object under investigation, toward a less oxidizing potential. In other words, the current flow through the environment forces pipe 101 to assume a negative electrical polarity with regard to the environment.

For cathodic protection, semi-permanent reference electrode 100 is placed on the earth's surface directly above the pipe 101. Semi-permanent reference electrode 100 is connected to the positive terminal of a voltmeter 102, the negative terminal of the voltmeter 102 being connected to pipe 101. Voltmeter 102 measures the potential difference between the pipe 101 and the semi-permanent reference electrode 100 to determine whether full cathodic protection has been obtained. Potentials on pipe 101 which are less negative indicate less than full cathodic protection while potentials which are more negative indicate more cathodic protection or wasted energy. The results of the potential measurement for rates of corrosion or the extent of cathodic protection can be recorded with a computer 103. An external power supply 104 is provided to supply a potential to the pipe 101 if necessary.

For purposes of the present invention, a counter electrode (not shown) may be utilized. The role of the counter electrode is to receive a majority of the current, rather than the current flowing directly from the working electrode, or pipe 101, to the semi-permanent reference electrode 100, so that only a small amount of the current flows from the pipe 101 to the semi-permanent reference electrode 100. This would alleviate concerns about high currents possibly flowing through the semi-permanent reference electrode 100 and possibly damaging it.

FIG. 2 is a cross section view of the preferred embodiment of the semi-permanent reference electrode 100. Semi-permanent reference electrode 100 is composed of an outer electrode body 105 which is generally cylindrical having openings at both ends, one end being sealed with a cap 109 and the other end sealed with a porous plug 106. Outer electrode body 105 is formed from any inert material that resists corrosion, such as but not limited to, glass, Teflon, polycarbonate, and polypropylene. Non-breakable materials are preferred for field application. Cap 109 can be of any inert material, such as but not limited to, Teflon and rubber.

Porous plug 106 is provided to maintain the internal environment of semi-permanent reference electrode 100 and to minimize either contamination of the semi-permanent reference electrode 100 by the environment or the environment by the semi-permanent reference electrode 100, while still allowing the passage of electrons. Porous plug 106 can be a porous frit or other membrane standard in the industry, such as, but not limited to, porous zirconia and porous alumina.

Fill solution 107 is contained within outer electrode body 105. The fill solution 107 of the present semi-permanent reference electrode 100 is formed from a solid salt and is maintained in solution in the field by way of moisture from the environment. The solid salt of fill solution 107 has two key properties. First, the solid salt used to form fill solution 107 is hygroscopic, that is, an essential property of the solid salt of the fill solution 107 is that it be able to take up water from the surrounding atmosphere. Further to this hygroscopic characteristic, the solid salt of the fill solution 107 must have a low deliquescence point, that is, the relative humidity at which the solid salt of the fill solution 107 takes up water and is in equilibrium with fill solution 107 should be relatively small to allow maintenance of the fill solution 107 as a saturated salt solution and operation of the semi-permanent reference electrode 100 in various field environments.

The fill solution 107 must also have a constant pH since the measured potential is pH dependent. Therefore, the second key characteristic of the solid salt of the fill solution 107 is that it be hydrolyzable, that is, capable of undergoing hydrolysis or chemical reaction with water. The solid salt which forms the fill solution 107 of the present invention can include, but is not limited to, salts of magnesium, calcium, zinc and iron such as magnesium chloride or sodium magnesium acetate.

An opening 110 is provided through cap 109 to allow moisture from the external environmental to penetrate into the fill solution 107 for maintenance of the solution. Wire 108 penetrates cap 109 with one end situated in the fill solution 107 and the other end connected to voltmeter 102 (See FIG. 1). Due to the nature of fill solution 107 and the field environment, wire 108 must maintain a relatively stable reference point in a wide array of environments and must not corrode at a high rate. Wire 108 includes, but is not limited to, oxidized tungsten and oxidized iridium.

In FIG. 3 an exploded view of the present semi-permanent reference electrode 100 is shown having an outer electrode body 105 which is generally cylindrical having openings at both ends, one end having a cap 109 and the other end continuous into a funnel section 111 and having a porous plug 106. Cap 109 preferably threads within one end opening of outer electrode body 105; however, other types of caps may be used that do not utilize threads.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A semi-permanent reference electrode for use in field applications, said semi-permanent reference electrode being associated with a working electrode to form a cell, said semi-permanent reference electrode and said working electrode being used in a system with a voltmeter, said voltmeter used to measure the potential difference between said working electrode and said semi-permanent reference electrode, and a power supply, said power supply being used to supply a potential to said working electrode, said semi-permanent reference electrode comprising:

an electrode body forming an electrode internal chamber;
a fill solution contained within said electrode internal chamber, said fill solution being a saturated salt solution with a constant pH formed from a solid salt, wherein said solid salt is hygroscopic, hydrolyzable and has a low deliquescence point;
a wire situated within said electrode internal chamber for making contact with said fill solution;
a cap removeably situated within said electrode inner chamber;
a porous plug removeably situated within said electrode inner chamber; and
an opening in said cap for passage of moisture from the environment into said electrode inner chamber;
wherein said fill solution does not dry in field applications because said fill solution can draw moisture from the environment to maintain itself in solution.

2. The semi-permanent reference electrode of claim 1 wherein said wire maintains a relatively stable reference point with a low rate of corrosion.

3. The semi-permanent reference electrode of claim 2 wherein said wire is an oxidized metal.

4. The semi-permanent reference electrode of claim 3 wherein said solid salt is selected from the group consisting of magnesium salt, calcium salt, zinc salt and iron salt.

5. The semi-permanent reference electrode of claim 4 wherein said solid salt is magnesium chloride or sodium magnesium acetate.

6. The semi-permanent reference electrode of claim 5 wherein said electrode body is formed from an inert material.

7. The semi-permanent reference electrode of claim 3 wherein said wire is formed from oxidized tungsten or oxidized iridium.

8. A method of using the semi-permanent reference electrode of claim 1 for measuring corrosion potential of a metallic object such as a pipeline, storage tank or bridge in a system utilizing a voltmeter, wherein said method comprises: placing said semi-permanent reference electrode directly above said metallic object; first connecting said semi-permanent reference electrode to said voltmeter; second connecting said voltmeter to said metallic object; and measuring the potential difference between said metallic object and said semi-permanent reference electrode to determine the corrosion potential of the metallic object.

9. The method of claim 8 wherein said solid salt is selected from the group consisting of magnesium salt, calcium salt, zinc salt, and iron salt.

10. A method of using the semi-permanent reference electrode of claim 1 for measuring potential of a cathodically protected metallic object such as a pipeline, storage tank or bridge in a system utilizing a voltmeter, wherein said method comprises the steps of:
producing a current flow onto said metallic object for cathodic protection to form a cathodically protected metallic object;
placing said semi-permanent reference electrode directly above said cathodically protected metallic object;
first connecting said semi-permanent reference electrode to said voltmeter;
second connecting said voltmeter to said cathodically protected metallic object;
and measuring the potential difference between said cathodically protected metallic object and said semi-permanent reference electrode to determine whether full cathodic protection for said metallic object has been obtained.

11. The method of claim 10 wherein said solid salt is selected from the group consisting of magnesium salt, calcium salt, zinc salt, and iron salt.

* * * * *